United States Patent [19]

Mahler

[11] 4,068,706

[45] Jan. 17, 1978

[54] THERMAL STABILIZATION OF CHLOROBENZENES

[75] Inventor: Walter Mahler, Wilmington, Del.

[73] Assignee: E. I. Du Pont de Nemours and Company, Wilmington, Del.

[21] Appl. No.: 677,444

[22] Filed: Apr. 15, 1976

Related U.S. Application Data

[63] Continuation-in-part of Ser. No. 470,636, May 16, 1974, abandoned, which is a continuation-in-part of Ser. No. 365,274, May 30, 1973, abandoned.

[51] Int. Cl.² .................. C09K 5/04; C09K 15/02; C07C 25/04; C07C 25/10
[52] U.S. Cl. .................................. 165/1; 252/67; 252/68; 252/397; 252/400 R; 260/650 R
[58] Field of Search ........ 260/650 R, 651 R, 652.5 R; 252/68, 75, 67, 400 R, 399, 397

[56] References Cited

U.S. PATENT DOCUMENTS

| 2,036,274 | 4/1936 | Holler | 260/650 R |
|---|---|---|---|
| 2,096,735 | 10/1937 | Dinley | 260/652.5 R |
| 2,542,216 | 2/1951 | Somogyi | 260/651 R |
| 2,630,442 | 3/1953 | Church | 260/651 R X |
| 2,945,895 | 7/1960 | Burch et al. | 260/652.5 R |
| 3,802,185 | 4/1974 | Tullock | 252/67 X |
| 3,944,494 | 3/1976 | Mahler | 252/68 |

*Primary Examiner*—Harris A. Pitlick

[57] ABSTRACT

Chlorobenzenes with 2 to 5 chlorine substituents particularly trichlorobenzenes, can be used in a heat transfer method, particularly when contained in steel or aluminum vessels and at temperatures in the range of 260°-450° C, by contact with a thermal stabilizing amount of a solid acid acceptor selected from a. a carbonate, phosphate, borate, or molybdate of an alkali metal or an alkaline earth metal or
b. an oxide of zinc, cadmium or an alkaline earth metal.

17 Claims, No Drawings

THERMAL STABILIZATION OF CHLOROBENZENES

RELATED APPLICATIONS

This application is a continuation-in-part of copending application Ser. No. 470,636, filed May 16, 1974, now abandoned, which is a continuation-in-part of Ser. No. 365,274 filed May 30, 1973, now abandoned.

BACKGROUND OF THE INVENTION

This invention relates to the thermal stabilization of chlorobenzenes, particularly in the presence of engineering metals.

THE PRIOR ART

Chlorinated benzenes have been prepared as heat exchange fluids heretofore. In particular, Buss, et al., U.S. Pat. No. 3,234,734 and Tabor U.S. Pat. No. 3,040,528 teach the use of chlorinated benzenes as the working fluid in Rankine cycle engines. Efficient utilization for this purpose demands the use of high boiler temperatures. Since the thermal stability of the chlorinated benzenes is rather poor in contact with engineering metals at elevated temperatures, the useful life of the chlorinated benzenes or the efficiency of the engines is severely limited. Accordingly, a method of stabilizing chlorobenzenes at useful boiler temperatures is needed.

SUMMARY OF THE INVENTION

The present invention is an improved method of heat transfer wherein at least one chlorobenzene of the formula $C_6H_{6-x}Cl_x$ where x is 2 to 5, cycled through a thermal gradient including temperatures above about 260° C, particularly while contained in metals such as ferritic steels, austenitic steels, and aluminum, which comprises contacting said chlorobenzene with a thermal stabilizing amount of a solid acid acceptor selected from:

a. a carbonate, phosphate, borate or molybdate of a Group IA alkali metal of atomic number 3-55, or a Group IIA alkaline earth metal of atomic number 12-56, or a b. an oxide of a Group IIA alkaline earth metal of atomic number 12-56 or a Group IIB metal of atomic number 30-48.

DETAILED DESCRIPTION OF THE INVENTION

The present invention is an improved method of heat transfer using polychlorobenzenes thermally stabilized with one or more of the described solid acid acceptor stabilizers. The stabilizers herein described are effective in glass, but more importantly they are effective when the liquids are in contact with typical engineering metals, particularly ferritic steels and aluminum and to a lesser extent in austenitic steels.

The beneficial effect of the stabilizers disclosed herein is of principal utility for those chlorobenzenes boiling between 150° and 277° C. Chlorobenzene, $C_6H_5Cl$, with a boiling point of 132° C is not generally applicable under the high temperature conditions where thermal decomposition becomes critical. Hexachlorobenzene, boiling around 322° C, has a liquid range that is quite small and too high for most applications.

The stabilizers disclosed herein for reducing the thermal decomposition of chlorobenzenes are all known to be acid acceptors. While the exact mode of operation of these stabilizers is unknown it is believed that they operate in part by removal of acidic chlorides such as $AlCl_3$ or $FeCl_3$ which may be formed early in the decomposition sequence and may catalyze further decomposition. However, the stabilizers are also effective in the absence of metal so that other mechanisms may also be important.

The new method is most beneficial with metallic heat transfer devices at temperatures in the range 260°–450° C. Under these conditions most commercial heat transfer fluids undergo rapid thermal decomposition as well as being extremely corrosive to metals. Alternatively, the stabilizers may be used at lower temperatures where the benefits are realized in longer periods before buildup of impurities in the fluids or corrosion of the heat transfer surfaces require maintenance operations.

In one aspect of the invention, the stabilizers disclosed herein greatly reduce the formation of the higher boiling and more hazardous polychlorinated biphenyl compositions that result from thermal decomposition of the chlorobenzenes. In another aspect, these stabilizers and particularly the alkali metal phosphates greatly reduce the corrosive attack of the chlorobenzenes on aluminum, a metal which has heretofore been considered too corrosion prone for the use with chlorobenzene heat transfer fluids.

The heat transfer is not impaired by the presence of water (up to 2%) when a chlorobenzene with one of the stabilizers is used. In the absence of these additives, water often accelerates the decomposition and corrosion of the halobenzenes. Surprisingly, the thermal stability of chlorobenzene with the additional presence of water is even greater in many instances than in the presence of the anhydrous stabilizer. Accordingly, commercial chlorobenzenes can be employed in the method of the present invention without dehydration.

It is preferred to keep the water content below about 2% based on the chlorobenzene fluid and generally from 0.005 to 1% in order to avoid a high partial pressure of water vapor in the heat exchange device and the possibility of direct corrosive attack by water. The water may be added directly to the chlorobenzene where it can be present either dissolved or as a separate phase (1,2,4-trichlorobenzene dissolves up to 0.026% water at 25° C). Alternatively the water may be provided by the addition of a hydrated borate such as borax, $Na_2B_4O_7.10 H_2O$.

It is believed that thermal decomposition and corrosive attack upon metals under heat transfer conditions occurs primarily in the liquid phase rather than in the saturated vapor phase. However, these stabilizers are effective even when contact is limited to the vapor phase. The stabilizers may be used as powders or pellets distributed throughout the liquid volume or they may be confined to a separate region through which the liquid or vapor flows. Alternatively the stabilizing additive may be present as a coating on the metal surface. Such a coating provides intimate contact at an effective site, but it may also reduce the efficiency of heat transfer. Still another method of stabilizer disposition is to form the solid, with binders if necessary, into a shaped article such as an open grid which can then be fired to form a self-supporting shape appropriate to the configuration of the heat transfer system. The optimum distribution of the stabilizer can readily be determined for any of the wide range of heat transfer configurations in which such fluids are used.

The amount of stabilizer needed to provide adequate protection against thermal decomposition can be quite small and will in general depend upon its distribution and on the use conditions. A significant improvement in stability can be measured whenever the bulk temperature of the liquid is at least about 260° C. Amounts of the order of one percent by weight of the heat transfer fluid are usually adequate even at liquid temperatures as high as 400° C. For less severe use conditions amounts as small as one tenth percent or less are useful for improving thermal stability.

The fact that the acid acceptors disclosed herein as stabilizers are generally effective for each of the individual chlorobenzenes indicates that they will also be useful for mixtures of several chlorobenzenes such as the isomer mixtures which may provide particular advantage e.g. by eliminating special purification steps in their synthesis, or by lowering the melting point. Similarly mixtures of one or more chlorobenzenes with other heat-stable fluids may benefit from the stabilizers disclosed herein.

The stabilizers of the present invention are all well known, and for the most part inexpensive and readily available. The term "oxide" as used in this specification does not include peroxides which are undesirable. The term "phosphate" includes condensed phosphates and polyphosphates as well as the simple phosphates such as $Na_3PO_4$, $Na_2HPO_4$ and $NaH_2PO_4$.

The inherent thermal stability of the polychlorinated benzenes will vary, of course, among the particular position isomers. For example, among the trichlorobenzenes, the 1,3,5-isomer is clearly the most stable, the 1,2,3-isomer the least stable, and the 1,2,4-isomer of intermediate stability, whether the stability at 400° C be judged by the formation of polychlorinated biphenyls from the pure liquid or by the extent of attack of the liquid upon a metal in contact with it. The extent of benefit of the various stabilizers may also differ from isomer to isomer and also depends on the different container materials and whether or not water is present.

One embodiment of the invention is the method of heat transfer using chlorobenzenes with a stabilizer comprising an alkali or alkaline earth metal carbonate or phosphate or ZnO in the presence of a ferritic iron surface. In heat transfer devices of plain carbon or low alloy steel it is preferred to use a fluid comprising 1,2,4-trichlorobenzene containing 0.05 -2.0 percent water in contact with an alkali metal borate. When a heat transfer apparatus is used as a power source a still more preferred method uses an externally fired boiler of high chromium (<10% Cr) ferritic steel in which the heat transfer fluid is 1,2,4-trichlorobenzene containing 0.01 to 0.50 percent water in contact with an alkali metal borate at a temperature from about 260° C to about 400° C. Austenitic steel surfaces are also protected from corrosion by these additives although they are less preferred for such applications because of their well-known susceptibility to attack by chlorine-containing media.

This invention is further illustrated by the following specific examples.

EXAMPLE I

A small coupon of aluminum weighing approximately 0.20 g was sealed into each of two Pyrex glass tubes containing about 1 g of 1,2,4-trichlorobenzene. The metal coupon in each was completely immersed in the liquid. One of the tubes also contained 0.1 g CaO. Both tubes were kept in an oven held at 400° C. After four days the tube without CaO showed evidence of major attack of the liquid on the aluminum whereas the contents of the tube containing CaO were unchanged in appearance. The tube without CaO was then cooled to about 25° C and gave an indication of high gas pressure when opened; the aluminum coupon showed a weight loss of 89.8 mg after washing, lightly rubbing with a paper towel to remove the superficial coating, and drying.

The tube containing CaO was kept at 400° C without any visible change of the Al until after 28 days it was cooled to −196° and then opened in an evacuated system. Even after warming to 25° the pressure rise was less than 1mm Hg, indicating no significant amount of gaseous decomposition products. The aluminum showed little weight change (0.3 mg gain) when treated and measured in the same way as described above for the unstabilized fluid.

EXAMPLE 2

In a manner similar to that of Example 1, coupons weighing about 0.2 g each were sealed into 2 cc Pyrex glass tubes containing 0.3 cc of 1,2,4-trichlorobenzene and 0.05 g of various inorganic solids to be tested as stabilizers. Sample tubes were kept at 400° C and were periodically examined for visual evidence of decomposition. When pure fluid without stabilizer was tested in this manner no change was apparent until after three days, when the completely black appearance of the contents of the tube indicated sudden and extensive reaction. With the following stabilizers present (0.05 g per gram of liquid) no visual change was noted after 28 days at 400° C when the tests were discontinued: $CaCO_3$, $Na_2CO_3$, $Na_3PO_4$, $Na_5P_3O_{10}$, $Na_2B_4O_7$, MgO, CaO and SrO. With 5% $K_2CO_3$ the liquid began to darken on the 20th day indicating the start of some decomposition. With .02 g ZnO the sudden evidence of reaction occurred after fourteen days.

EXAMPLE 3

In a manner similar to that of example 2, Al coupons were contacted with water-saturated 1,2,4-tri-chlorobenzene (analysis showed 259 ppm $H_2O$) and 0.05 g $Na_2B_4O_7$. There was no significant change in appearance of the Al or the fluid after twenty-eight days at 400°. Without additive, complete decomposition of the fluid had occurred by the fifth day.

EXAMPLE 4

Aluminum remained clean in 1,2,4-trichlorobenzene at 350° for 198 days with added $CaCO_3$ or $Na_2B_4O_7$. Biphenyl formation at the end of that time was 0.07% for $CaCO_3$ and 0.12% for $Na_2B_4O_7$. In the absence of additive, 1,2,4-$C_6H_3Cl_3$ in the presence of Al was completely destroyed in 39 days at 350°.

EXAMPLE 5

In a manner similar to examples 1 and 2, 0.3 cc 1,2,4-$C_6H_3Cl_3$ was placed in a 2 cc tube with a coupon of type 5052 Al (2.5% Mg). The sealed tube was heated at 400° C and periodically inspected. After ten days the metal was slightly coated and the liquid appeared to be relatively unchanged. On the fourteenth day, the tube had exploded. The recovered metal coupon had lost 0.0716g.

A sample of plain Al(99.9%) under the same experimental conditions showed heavy deposits after two days and the tube exploded on the third day. The Al had lost 0.0620 g. The improved performance of the magnesium containing alloy is attributed to a surface layer of MgO.

EXAMPLE 6

Two coupons of type 5052 Al were placed in a 5% NaOH solution for ten minutes at 25°. They were rinsed with water and acetone and dried. This treatment was intended to increase the MgO content at the surface by selectively dissolving away Al.

A treated coupon was placed in .3 cc $1,2,4-C_6H_3Cl_3$ in a 2 cc tube and the tube sealed and heated at 400° C. After seventeen days the metal and the liquid appeared to be little changed, but by the twentieth day, the tube contents were entirely black and no liquid could be seen.

Another treated coupon of type 5052 Al was placed in .3 cc $1,2,4-C_6H_3Cl_3$ in a 2 cc tube together with a coupon of plain Al. After four days at 400° C both coupons and the liquid appeared to be little changed. On the fifth day there appeared to be extensive decomposition; however, on opening the tube there was no pressure.

These tests indicate that an increased MgO layer offers added stability.

EXAMPLE 7

In a similar manner, 0.3 cc $1,2,4-C_6H_3Cl_3$ was placed in a 2 cc tube with a coupon of type 7075 Al (2.5% Mg, 5.6% Zn, 1.6% Cu) weighing 0.4265 g. The sealed tube was heated at 400° C and periodically inspected. After twenty-eight days the metal was slightly coated and the liquid was a clear light brown. After the tube was opened (no pressure) it was found that the 7075 Al coupon had gained 0.0012 g and the fluid contained 0.55% biphenyls. The improved stability is attributed to ZnO and MgO on the metal surface.

EXAMPLE 8

When tested by the method of Example 2 pure 1,2-dichlorobenzene in contact with aluminum failed after one day at 400° C. When the 1,2-dichlorobenzene contained 5% of $CaCO_3$ no failure occurred within twentyeight days.

EXAMPLE 9

When tested by the method of Example 2, pure 1,2-dichlorobenzene in contact with aluminum at 350° failed in less than twenty-seven days. 1,3-dichlorobenzene failed in less than 74 days. In the presence of added (5%) $Na_2CO_3$ Al suffered no weight loss at 350° in 188 days with 1,2- 1,3- or 1,4-dichlorobenzene. Biphenyl formation after 188 days amounted to 1.7% for the orthoisomer, 1.4% for meta and 0.18% for para.

EXAMPLE 10

When tested by the method of Example 2 pure 1,3-dichlorobenzene in contact with aluminum failed after 2 days at 400° C. When the 1,3-dichlorobenzene contained 5% of $CaCO_3$ or $Na_2CO_3$ no failure occurred within twenty-eight days.

EXAMPLE 11

When tested as in Example 2 pure 1,4-dichlorobenzene failed after 1 day at 400° C but did not fail within twenty-eight days in the presence of 5% of $CaCO_3$.

EXAMPLE 12

When 1,2,4-trichlorobenzene is held in contact with steels at 400° C there appears to be no delay until the onset of reaction as is the case for contact with aluminum. The extent of decomposition can be measured by the weight change of a steel coupon as well as by the impurity build-up in the fluid. The extent of formation of biphenyl derivatives can readily be measured by gas chromatography to give an indication of decomposition of the chlorobenzene fluids both in the presence and absence of a metallic coupon. 1.2.4-Trichlorobenzene 1,2,4-Trichlorobenzene was maintained in the liquid state at 400° C in Pyrex glass tubes for 7 days in the absence of any metal and in the presence of 1018 steel (carbon steel), P-11 steel (a low alloy steel, 1.3% Cr, 0.5% Mo) 430 stainless steel (17% Cr), 304 stainless steel (18% Cr, 10% Ni) and "26-1" (26% Cr, 1% Mo). Specifically, 1.0 g of 1,2,4-tri chlorobenzene and 0.05 g of stabilizer was used with a metal test coupon weighing approximately 2 g and having a nominal surface (measured as though the surface were perfectly smooth) of approximately 3 $cm^2$ in a Pyrex glass tube having an internal volume of 3 cc. Under these conditions the metal coupon is completely covered by the liquid at 400° C. The coupon was weighed to the nearest 0.1 mg and its surface measured to the nearest 0.1 $cm^2$ before the test. Afterward, the metal coupon was rinsed first with acetone, then water and freed of adhering coatings with a paper towel and rinsed again with water and then acetone, dried and weighed to the nearest 0.1 mg. The "corrosion" corresponds to the weight loss of the metal coupon in mg per $cm^2$ of metal per g of test fluid. The liquid was analyzed by gas chromatography and the sum of the biphenyls expressed as a percent of the initial chlorobenzene. The results are shown in Table I. Each of the indicated stabilizers is effective in reducing the thermal decomposition of trichlorobenzene. Group II oxides, alkali, and alkaline earth carbonates and phosphates are particularly effective in stabilizing in the presence of chromium bearing stainless steel.

TABLE I

| | Decomposition of 1,2,4-Trichlorobenzene at 400° C for Seven Days | | | | | | | | | | |
|---|---|---|---|---|---|---|---|---|---|---|---|
| | A. Biphenyl Formation* | | | | | | B. Corrosion** of | | | | |
| Stabilizer | No Metal | 1018 Steel | P-11 Steel | 304 S. Steel | 430 S. Steel | 26-1 | 1018 Steel | P-11 Steel | 304 S. Steel | 430 S. Steel | 26-1 S. Steel |
| None | 4.6 | 13.2 | 5.4 | 3.0 | 4.1 | 10.7 | 17.8 | 8.0 | 22.0 | 6.0 | 12.0 |
| $CaCO_3$ | 1.2 | 3.7 | 0.93 | — | 0.37 | 1.6 | 7.2 | 0.94 | — | 0.00 | 0.00 |
| $Na_2CO_3$ | 0.49 | 1.0 | 1.1 | 0.42 | 0.28 | 2.7 | 0.64 | 0.00 | 0.00 | 0.00 | 0.00 |
| $K_2CO_3$ | 0.20 | — | — | — | — | — | — | — | — | — | — |
| $Li_2CO_3$ | 0.29 | 12.7 | 7.5 | — | 0.18 | — | 8.3 | 4.7 | — | 0.0 | — |
| $LiBO_2$ | — | — | — | — | — | 2.0 | — | — | — | — | 0.00 |
| $Na_3PO_4$ | 0.002 | — | 2.7 | — | 1.7 | 1.2 | 10.5 | 6.6 | — | 1.4 | 0.00 |
| $Li_3PO_4$ | 0.79 | 2.2 | 5.9 | — | 2.8 | — | 6.2 | 4.3 | — | 3.9 | — |
| $K_4P_2O_7$ | 0.26 | — | — | — | — | 1.8 | — | — | — | — | 0.00 |
| $Na_5P_3O_{10}$ | 0.066 | 9.5 | 10.2 | — | 3.2 | — | 14.4 | 6.2 | — | 1.5 | — |
| $KPO_3$ | 1.9 | — | — | — | — | 5.2 | — | — | — | — | 8.2 |
| $Na_2P_6O_{13}$ | 0.04 | — | 4.4 | — | 0.70 | — | — | 7.8 | — | 0.08 | — |
| $Na_2MoO_4$ | 0.048 | 17.9 | — | — | 13.3 | 2.4 | 9.9 | 5.1 | — | 11.2 | 0.00 |

TABLE I-continued

| | Decomposition of 1,2,4-Trichlorobenzene at 400° C for Seven Days | | | | | | | | | |
|---|---|---|---|---|---|---|---|---|---|---|
| | A. Biphenyl Formation* | | | | | B. Corrosion** of | | | | |
| Stabilizer | No Metal | 1018 Steel | P-11 Steel | 304 S. Steel | 430 S. Steel | 26-1 | 1018 Steel | P-11 Steel | 304 S. Steel | 430 S. Steel | 26-1 S. Steel |
| MgO | 0.60 | 6.6 | 4.3 | — | — | 2.0 | 16.4 | 7.6 | — | — | 0.90 |
| CaO | 0.97 | 2.7 | 1.2 | — | 0.30 | — | 6.4 | 4.0 | — | 1.4 | — |
| ZnO | 0.008 | 6.6 | — | — | 0.54 | 0.48 | 10.2 | 8.0 | — | 1.2 | 0.00 |

*% of initial $C_6H_3Cl_3$ converted to biphenyl derivatives
**mg/cm² weight loss per g of $C_6H_3Cl_3$

EXAMPLE 13

The most effective stabilizers for 26-1 stainless steel at the 5% level from Table I were ZnO and $Na_3PO_4$. These were evaluated under the same conditions at lower quantities of additive (expressed as wt. % relative to $C_6H_3Cl_3$).

TABLE II

| Decomposition of 1,2,4-Trichlorobenzene at 400° for Seven Days in the Presence of 26-1 Stainless Steel | | |
|---|---|---|
| Stabilizer | Biphenyl Formation, % | Corrosion mgcm$^{-2}$g$^{-1}$ |
| None | 10.7 | 12.0 |
| 1.0% ZnO | 0.09 | 0.12 |
| 0.3% ZnO | 0.42 | 0.00 |
| 0.1% ZnO | 3.6 | 4.9 |
| 1.0% $Na_3PO_4$ | 0.30 | 0.03 |
| 0.3% $Na_3PO_4$ | 4.7 | 7.0 |
| 0.1% $Na_3PO_4$ | 2.7 | 8.6 |

EXAMPLE 14

The best additives of Table I for 26-1 stainless steel with 1,2,4-$C_6H_3Cl_3$ at 400° for 7 days were ZnO and $Na_3PO_4$. The conditions of Example 12 were repeated except the duration was twenty-eight days. There was no detectable weight loss of the steel with either additive, and biphenyl formation was 1.0% with ZnO and 1.4% with $Na_3PO_4$.

EXAMPLE 15

Under the conditions of Example 12 1,2,4-$C_6H_3Cl_3$ containing 5,700 ppm of water was tested with 26-1stainless steel and .05 g $Na_3PO_4$ at 400° for 7 days. There was no detectable corrosion and no formation of $H_2$, and biphenyl formation was 2.1%. With the same amount of water and no $Na_3PO_4$, the sample tubes exploded due to build up of $H_2$ pressure.

EXAMPLE 16

Various polychlorobenzenes were tested for 7 days at 400° C by the same procedure and the same concentrations used in Example 8. The results are shown in Table III.

TABLE III

Stabilizing Influence of $Na_2CO_3$ on Polychlorobenzenes* at 400° C for seven days

| Polychloro- | A. % Biphenyl | | B. Corrosion of 1018 | |
|---|---|---|---|---|
| benzene | pure | 5% $Na_2CO_3$ | pure | 5% $Na_2CO_3$ |
| 1,2-di | 2.3 | 0.13 | 9.2 | 10.6 |
| 1,3-di | 14.6 | 1.46 | 21.0 | 0.0 |
| 1,4-di | 1.1 | 0.12 | — | — |
| 1,2,3-tri | 24.0 | 2.9 | d** | d |
| 1,2,4-tri | 13.2 | 0.49 | 17.8 | 0.64 |
| 1,3,5-tri | 1.6 | 1.1 | 10.4 | 5.3 |
| 1,2,3,4-tetra | 15.6 | 0.0 | 13.0 | 3.4 |
| penta- | 1.7 | 1.5 | 8.6 | 12.0 |

*The degree and position of Cl substitution of benzene is indicated in the left column.
**extensive decomposition in the presence of steel

EXAMPLE 17

A 1 g sample of pentachlorobenzene with 26-1 stainless steel after 7 days at 400° showed a corrosion rate of 5.0 mgcm$^{-2}$ and 14.3% formation of biphenyls. Under the same conditions but with 5% added ZnO, corrosion was 3.9 mgcm$^{-2}$ and biphenyl formation 5.0%. With 5% $Na_3PO_4$, corrosion was 0.3 mgcm$^{-3}$ and biphenyl formation 1.3%. 5% $Na_2B_4O_7$ together with 0.3% $Na_2B_4O_7 \cdot 10H_2O$ in pentachlorobenzene resulted in 1.8 mgcm$^{-2}$ corrosion and 6.3% biphenyl formation.

EXAMPLE 18

Table IV shows the influence of varying amounts of $Na_2B_4O_7$ and water on the stability of 1,2,4-trichlorobenzene in contact with various steels for 7 days at 400° C. While the alkali metal borate is an effective stabilizer in anhydrous media, the presence of even small amounts of water dramatically increases the effectiveness. The minimum amount of water necessary for maximum stability varies with the type of steel: 1018 steel requires about 0.5%, P-11 requires about 0.05% and 26-1 stainless steel requires only about 0.015% water for maximun effect under the conditions of use in Table IV.

TABLE IV

| Stabilization of 1,2,4-Trichlorobenzene at 400° for Seven Days | | | | |
|---|---|---|---|---|
| Metal | $Na_2B_4O_7$ (%)* | $H_2O$ (%)* | Corrosion** | % Biphenyls |
| None | 0 | 0 | — | 2.7 |
| None | 0 | 0.026 | — | 2.3 |
| None | 5 | 0 | — | 0.92 |
| 1018 | 0 | 0 | 9.4 | 15.0 |
| 1018 | 0 | 0.026 | 9.3 | 4.8 |
| 1018 | 0 | 0.210 | 9.2 | 21.0 |
| 1018 | 0 | 0.800 | 5.8 | 14.3 |
| 1018 | 5 | 0 | 9.6 | 15.5 |
| 1018 | 5 | 0.026 | 9.2 | 8.0 |
| 1018 | 5 | 0.140 | 4.4 | 3.3 |
| 1018 | 5 | 0.470 | 0.00 | 1.4 |
| 1018 | 5 | 0.940 | 0.00 | 1.5 |
| 1018 | 5 | 1.400 | 0.00 | 1.2 |
| 1018 | 5 | 1.880 | 0.00 | 2.2 |
| P-11 | 0 | 0 | 13.0 | 9.4 |
| P-11 | 0 | 0.026 | 9.3 | 11.2 |
| P-11 | 0 | 0.240 | 3.8 | 12.3 |
| P-11 | 0 | 0.700 | 6.7 | 21.0 |
| P-11 | 5 | 0 | 27.0 | 11.0 |
| P-11 | 5 | 0.007 | 10.0 | 8.4 |
| P-11 | 5 | 0.026 | 10.0 | 2.2 |
| P-11 | 5 | 0.050 | 0.00 | 0.80 |
| P-11 | 5 | 0.140 | 0.00 | 2.0 |
| P-11 | 5 | 0.470 | 1.0 | 3.0 |
| P-11 | 5 | 0.940 | 0.60 | 2.9 |
| P-11 | 5 | 1.400 | 0.00 | 2.3 |
| 26-1 | 0 | 0 | 14.0 | 12.3 |
| 26-1 | 0 | 0.026 | 11.4 | 5.0 |
| 26-1 | 0 | 0.120 | 5.9 | 8.9 |
| 26-1 | 0 | 0.200 | 12.5 | >20.0 |
| 26-1 | 0 | 0.500 | 15.5 | >20.0 |
| 26-1 | 5 | 0 | 12.0 | 5.0 |
| 26-1 | 5 | 0.007 | 10.0 | 4.5 |
| 26-1 | 5 | 0.015 | 0.20 | 0.75 |
| 26-1 | 2 | 0.0260 | 0.09 | 0.55 |
| 26-1 | 5 | 0.026 | 0.00 | 0.75 |
| 26-1 | 5 | 0.046 | 0.00 | 1.1 |
| 26-1 | 5 | 0.140 | 0.00 | 1.9 |
| 26-1 | 5 | 0.470 | 0.00 | 2.5 |
| 26-1 | 5 | 0.940 | 0.00 | 1.7 |
| 26-1 | 5 | 1.400 | 0.00 | 2.0 |
| 430 | 0 | 0 | 16.2 | 5.1 |

TABLE IV-continued

Stabilization of 1,2,4-Trichlorobenzene at 400° for Seven Days

| Metal | $Na_2B_4O_{7\,(\%)}$* | $H_2O$ (%)* | Corrosion** | % Biphenyls |
|---|---|---|---|---|
| 430 | 5 | 0.500 | 0.00 | 1.8 |
| 304 | 0 | 0 | 22.0 | 3.0 |
| 304 | 5 | 0 | 0.00 | 0.25 |
| 304 | 5 | 0.500 | 0.00 | 1.6 |

*based on $C_6H_3Cl_3$
**mg (metal lost) $cm^{-2}$ (metal surface) per g $C_6H_3Cl_3$

EXAMPLE 19

1.0 of o-dichlorobenzene in contact with 26-1 stainless steel at 400° for 7 days showed a corrosion rate of 12.4 mgcm$^{-2}$ and biphenyl formation of 6.3%. With With anhydrous $Na_2B_4O_7$ (.05 g) the corrosion rate was 9.1 mgcm$^{-2}$ and biphenyl formation 8.2%. With 470 ppm $H_2O$ in the o-dichlorobenzene as well as .05 g $Na_2B_4O_7$, the corrosion rate was 0.00 mgcm$^{-2}$ and biphenyl formation 0.17%.

EXAMPLE 20

1.0 g of o-dichlorobenzene with 430 stainless steel at 400° for 7 days had a corrosion rate of 5.7 mgcm$^{-2}$ and biphenyl formation of 15.0%. With 0.05 g $Na_2B_4O_7$ added, the corrosion rate was 0.00 mgcm$^{-2}$ and the biphenyl formation was 1.6%.

EXAMPLE 21

A 1 g sample of 1,2,4-$C_6H_3Cl_3$ was placed in a 6 mm id Pyrex®-glass tube together with a completely immersed coupon of 26-1 stainless steel (26% Cr, 1% Mo, balance Fe). A glass rod supported in a ZnO pellet (.1 g) above the surface of the liquid. The pellet was made by pressing ZnO powder in a mold at 20,000 lb/in$^2$. The tube was sealed above the ZnO pellet giving an internal volume of 2 cc. After heating at 400° C for 7 days, the tube was opened. The metal coupon had lost 0.1 mg and the biphenyl analysis implied a 1.2% decomposition of starting material. 1,2,4-$C_6H_3Cl_3$ with 26-1 stainless steel in the absence of an additive heated under the same conditions resulted in a 30.4 mg loss of metal and 4.1% decomposition of the liquid.

What is claimed is:

1. In a method of heat transfer wherein at least one chlorobenzene of the formula $C_6H_{6-x}Cl_x$ 

where x is 2 to 5
is cycled through a thermal gradient including temperatures above about 260° C, the improvement which comprises contacting said chlorobenzene with a thermal stabilizing amount of a solid acid acceptor selected from
 a. a carbonate, phosphate, borate or molybdate of a Group I-A alkali metal of atomic number 3-55 or a Group II-A alkaline earth metal of atomic number 12-56, or
 b. an oxide of a Group II-A metal of atomic number 12-56 or a Group II-B metal of atomic number 30-48.

2. The method of claim 1 wherein said chlorobenzene is in contact with ferritic steel, austenitic steel or aluminum.

3. The method of claim 2 wherein water is present in an amount of from 0.005 to 1% by weight of said chlorobenzene.

4. Method of claim 3 wherein said chlorobenzene is trichlorobenzene and said trichlorobenzene is contacted with said acid acceptor at a temperature in the range of 260° C to 450° C.

5. Method of claim 4 wherein said stabilizer is sodium carbonate.

6. Method of claim 4 wherein said stabilizer is magnesium oxide.

7. Method of claim 4 wherein said stabilizer is zinc oxide.

8. The method of claim 2 wherein the chlorobenzene is contacted with said acid acceptor at a temperature in the range of 260° C to 450° C.

9. The method fo claim 8 wherein said chlorobenzene is trichlorobenzene.

10. Method of claim 9 wherein said stabilizer is sodium carbonate.

11. Method of claim 9 wherein said stabilizer is magnesium oxide.

12. Method of claim 9 wherein said stabilizer is zinc oxide.

13. Method of claim 8 wherein said chlorobenzene is dichlorobenzene.

14. Method of claim 13 wherein said stabilizer is sodium carbonate.

15. Method of claim 13 wherein said stabilizer is magnesium oxide.

16. In a method of heat transfer wherein at least one chlorobenzene selected from the class consisting of dichlorobenzene and trichlorobenzene is cycled through a thermal gradient including temperatures above about 260° C., the improvement which comprises contacting said chlorobenzene with a thermal stabilizing amount of a solid acid acceptor selected from the class consisting of sodium borate and $Na_3PO_4$, wherein said chlorobenzene is in contact with ferritic steel, austenitic steel or aluminum, and wherein said chlorobenzene is contacted with said acid acceptor at a temperature in the range of about 260° C to 450° C.

17. The method of claim 16 wherein said chlorobenzene is trichlorobenzene and wherein water is present in an amount of from 0.005 to 1% by weight of said chlorobenzene.

* * * * *